(12) United States Patent
Lang et al.

(10) Patent No.: US 6,682,548 B2
(45) Date of Patent: Jan. 27, 2004

(54) MEDICAL INSTRUMENT

(75) Inventors: Dieter Lang, Stockheim (DE); Thomas Hopf, Stockheim (DE); Michael Strobel, Mitterfels (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 10/314,579

(22) Filed: Dec. 9, 2002

(65) Prior Publication Data

US 2003/0139757 A1 Jul. 24, 2003

Related U.S. Application Data

(63) Continuation of application No. PCT/EP01/06427, filed on Jun. 7, 2001.

(30) Foreign Application Priority Data

Jun. 10, 2000 (DE) .......................................... 100 28 896

(51) Int. Cl.⁷ .......................... A61B 17/28; A61B 17/42; A61B 17/44
(52) U.S. Cl. ........................ 606/205; 606/206; 606/207; 606/208
(58) Field of Search ................................. 606/205, 206, 606/207, 208, 210, 174, 51, 52; 600/104; 81/4, 5

(56) References Cited

U.S. PATENT DOCUMENTS 4,655,216 A * 4/1987 Tischer .................. 128/303.17
4,712,545 A 12/1987 Honkanen .................... 128/305
5,308,358 A 5/1994 Bond et al. .................. 606/205
5,997,565 A * 12/1999 Inoue .......................... 606/205
6,447,532 B1 * 9/2002 Herder et al. ................ 606/208

FOREIGN PATENT DOCUMENTS

| DE | 198 33 600 A1 | 3/2000 |
| EP | 0 668 057 A2 | 8/1995 |
| WO | WO 98/11833 | 3/1998 |

* cited by examiner

*Primary Examiner*—Michael J. Milano
*Assistant Examiner*—Charles H. Sam
(74) *Attorney, Agent, or Firm*—St. Onge Steward Johnston & Reens LLC

(57) ABSTRACT

A medical instrument with a hollow shaft having at its proximal end a handle consisting of at least two gripping members and at its distal end a tool consisting of at lest two jaw members, where at least one jaw member of the tool is adjustable in relation to the at least one other jaw member of the tool for purposes of opening and closing by means of one rotatably shaped gripping member of the handle, and the at least one adjustable jaw member and the corresponding gripping member of the handle that serves to adjust the jaw member are connected to one another by means of two push-pull rods. In order to create a medical instrument that ensures a constantly sufficient transmission of power, it is proposed with the invention that the two push/pull rods are secured on contact points at intervals from one another above and below the pivot point of the adjustable jaw member on this jaw member in such a way that two straight lines each extending from the pivot point through one of the contact points form an angle (alpha+beta) of 110 to 160 degrees.

7 Claims, 4 Drawing Sheets

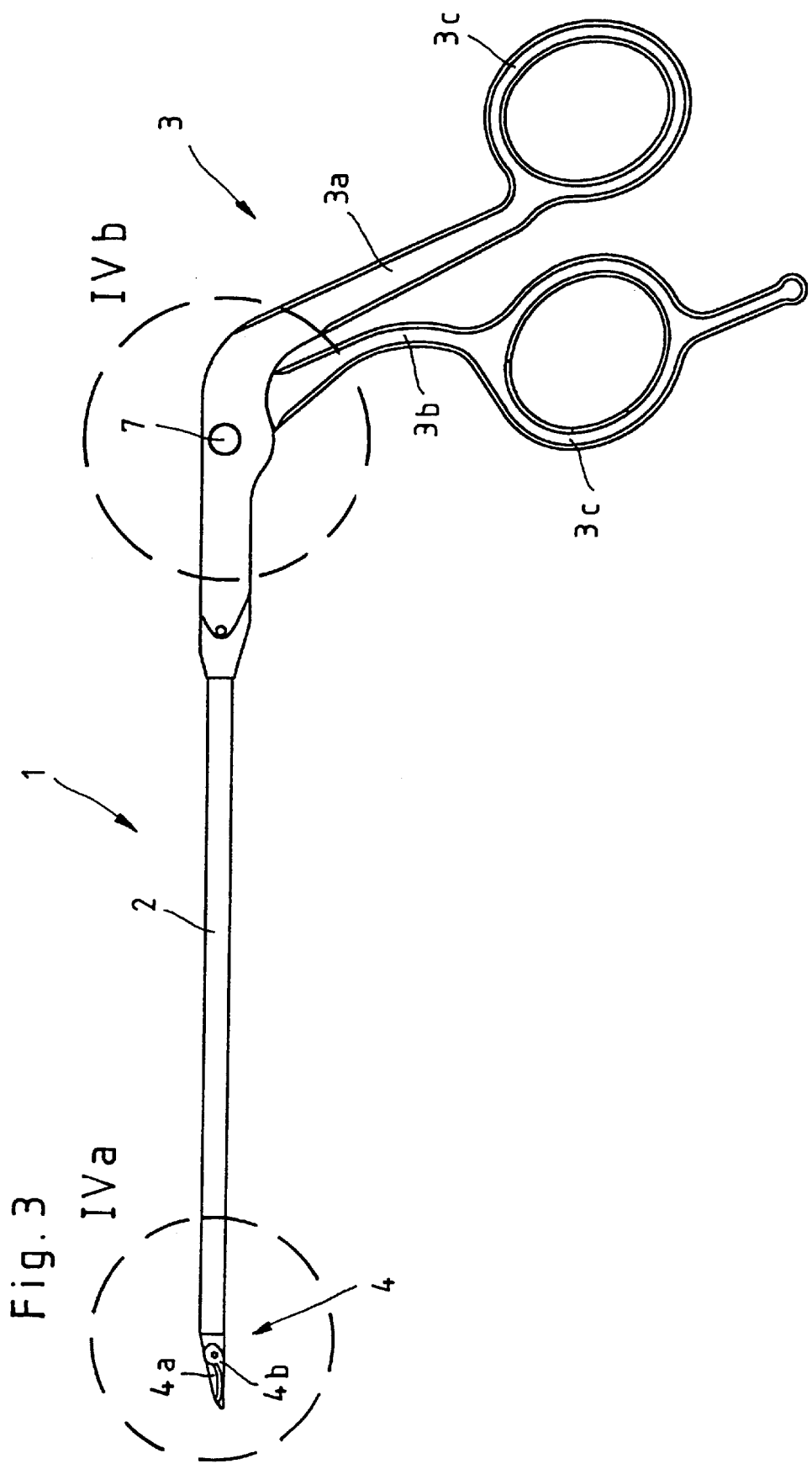

MEDICAL INSTRUMENT

This application is a continuation of pending International Patent Application No. PCT/EP01/06427 filed Jun. 7, 2001, which designates the United States and claims priority of pending German Application No. 100 28 896, filed Jun. 10, 2000.

FIELD OF THE INVENTION

The invention relates to a medical instrument with a hollow shaft having at its proximal end a handle consisting of at least two gripping members and at its distal end a tool consisting of at lest two jaw members, where at least one of the jaw members of the tool is adjustable in relation to the at least one other jaw member of the tool for purposes of opening and closing by means of one rotatably shaped gripping member of the handle, and the at least one adjustable jaw member and the corresponding gripping member of the handle that serves to adjust the jaw member are connected to one another by means of two push-pull rods.

Conventional instruments couple the movable jaw member or the movable jaw members by means of a lever mechanism. Here the angle between the instrument's axis and the line through the pivot point of the jaw member and of the contact point on the lever is selected to be as wide as possible. In opening or closing the jaw members, the angle is forcibly reduced, however, and thus the transmission of power is clearly worsened. Particularly in medical punches for tissue, it is unclear what is the optimal angle of the jaw members that is required for transmitting power, since there can be various tissue thicknesses to deal with.

A conventional medical instrument is known from WO 98/1183 A2. In this familiar medical instrument configured as a forceps, the adjustable forceps member is connected with the rotatable gripping members of the handle by two push/pull rods, which are situated bilaterally on the rollers of a roller bearing, and the rollers are rigidly connected with the rotatable gripping member or the adjustable forceps member. The contact points of the push/pull rod are positioned on the roller of the adjustable forceps member in such a way that these points lie on a straight line above and below the pivot point of the adjustable forceps member, which straight line runs through the pivot point and these contact points.

Because of this 180-degree angle that extends between the two contact points along this straight line, it is inevitable that in the open or closed position of the adjustable forceps member, one of the angles applicable to the lever ratio must be clearly greater than 90 degrees between the longitudinal axis of the medical instrument and a line running through the pivot point of the adjustable forceps member and the contact points of the push/pull rods on the roller. The ideal lever ratio proves to be 90 degrees. The greater the angle—that is, the farther the force parallelogram is extended—the more favorable are the lever ratios for transmitting power.

Another instrument is known from U.S. Pat. No. 4,712, 545 A. In this familiar surgical instrument, the movable jaw member is conducted on a curved track in the stationary portion of the shaft and on an additional curved track toward the push pin. This configuration leads to imaginary pivot points that lie partly outside the instrument's shaft. Through this method, however, only the lever arm is enlarged—similar effects can be achieved by such methods on the handle—and thus in every position more power is transmitted. However, the more the force parallelogram is extended, the more favorable the lever ratio becomes, so that in an extreme case even with a large lever arm no further power can be transmitted.

On the basis of this state of the art, the object of the invention is to make an improved medical instrument of the aforementioned type in such a way that it will ensure an always sufficient application of power onto the closing of the jaw members.

This object is achieved by means of the invention in that the two push/pull rods are secured on contact points at intervals from one another above and below the pivot point of the adjustable jaw member on this jaw member in such a way that two straight lines each extending from the pivot point through one of the contact points form an angle of 110 to 160 degrees.

Because the invention limits the angle between the two contact points to 110 to 160 degrees, it is possible to situate the position of the contact points of the push/pull rod on the adjustable jaw member and of the pivot point of the adjustable jaw member to one another in such a way that the angles alpha and beta between the longitudinal axis of, the medical instrument and a line through the contact points of the push/pull rod on the adjustable jaw member, both in the open position and also in the closed position, are each 90 degrees and thus ensure a virtually ideal lever ratio for a constantly sufficient transmission of power.

The result of this arrangement is that upon opening the jaw members, one push/pull rod is activated to push and the other rod to pull. Upon closing the jaw members, the functioning of the push/pull rod is correspondingly reversed. The use of one push/pull rod activated to push and one to pull also allows the penetration through tough tissue without the danger that an uncontrolled thrust occurs during penetration because of the sudden release of the resistance, since the transmission of power is always controllable because of the constantly favorable lever ratios.

In order to be able to clean the inventive medical instrument properly, and to make possible simple and rapid repairs, it is further proposed that the instrument should be constructed so that it can be dismantled.

In an initial embodiment of the invention, it is proposed that the push/pull roads should be dissolubly connected with the respective gripping member of the handle by means of a groove connection, in particular a spring-activated groove connection. In this manner the push/pull rods can then be pivoted out of the shaft together with the movable handle.

In another embodiment of the invention it is proposed that the tool should be secured on the distal end of the shaft by means of a bayonet coupling and the push/pull rods should be dissolubly attached on the movable gripping member.

In addition to using a common shaft for all push/pull rods, in an alternate embodiment it is proposed that every push/pull rod should be contained in a separate hollow shaft.

To reduce the rotation path of the gripping members of the handle toward one another, the handle can be equipped with a transmission so that the overall mobility of the instrument is increased.

Finally, it is proposed with this invention that the at least two jaw members of the tool should be configured to be adjustable by means of two push/pull rods each, so that each jaw member can be actuated by means of a separate gripping member of the handle. This configuration of the inventive medical instrument has the advantage that the jaw members can also be closed at various angle settings to the shaft.

BRIEF DESCRIPTION OF DRAWINGS

Other features and advantages of the invention derive from the following description of the associated illustrations, in which one embodiment of an inventive medical instrument is presented by way of example. The illustrations are as follows:

FIG. 3 is a side elevation of the medical instrument according to FIG. 1 but showing the jaw members in the closed position;

DETAILED DESCRIPTION OF DRAWINGS

Figure 1:
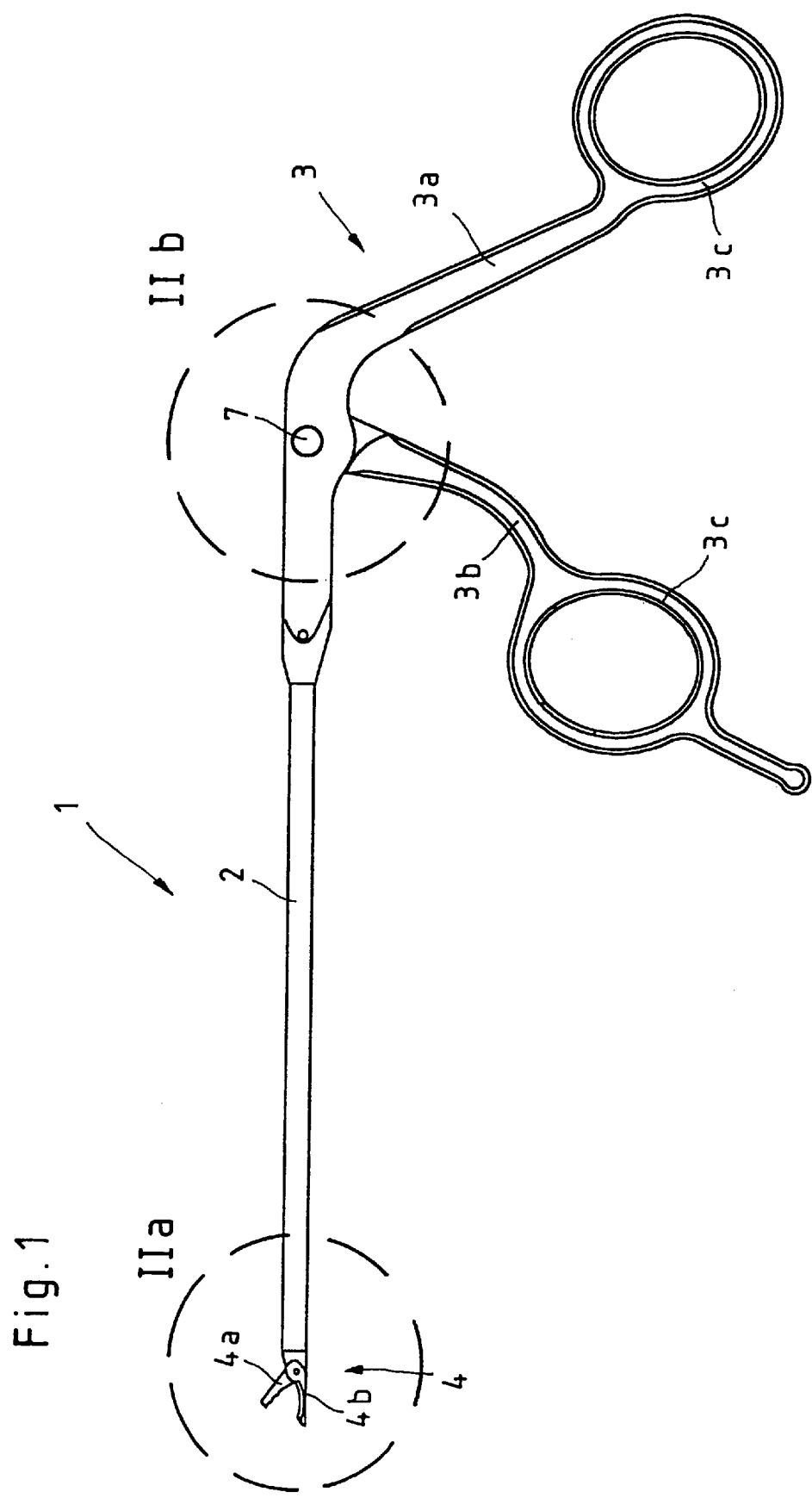
FIG. 1 is a lateral view of an inventive medical instrument showing the jaw members in the open position.

FIG. 1 and FIG. 3 show side elevations of a medical instrument 1, whose power transmission mechanism can be used in many ways, such as for punches, scissors, nail holders, gripping instruments, and the like.

The medical instrument 1 consists basically of a hollow shaft 2 on whose proximal end a handle 3 is mounted, which consists of a stationary gripping member 3a and a gripping member 3b that is rotatable in relation to the stationary gripping member 3a. At the distal end of the shaft 2, a tool 4 is mounted, which in the embodiment in the illustration has an adjustable jaw member 4a and a jaw member 4b that is rigidly connected with the shaft 2.

As can be seen from the detail views in FIGS. 2a, 2b and FIGS. 4a, 4b, the adjustable jaw member 4a of the tool 4 and the rotatable gripping member 3b of the handle 3 are connected with one another by means of two push/pull rods 5 in such a manner that the adjustable jaw member 4a can be moved from the closed position (FIGS. 3, 4a, and 4b) into the open position (FIGS. 1, 2a, and 2b) or vice versa by rotation of the gripping member 3b.

Figure 2A:
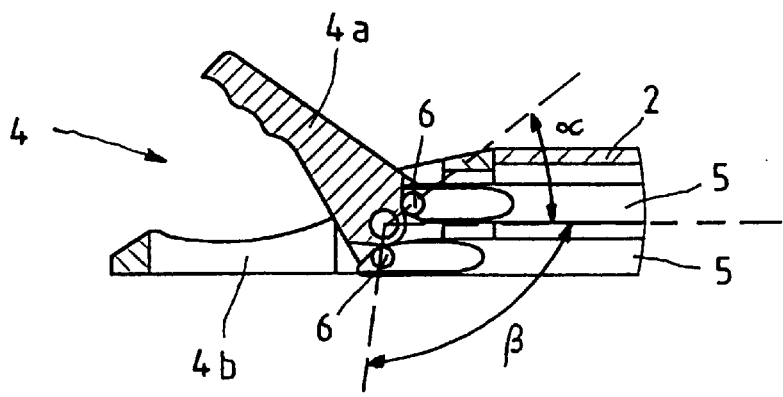
FIG. 2a is an enlarged and partially sectional view of the detail IIa according to FIG. 1.
Figure 2B:
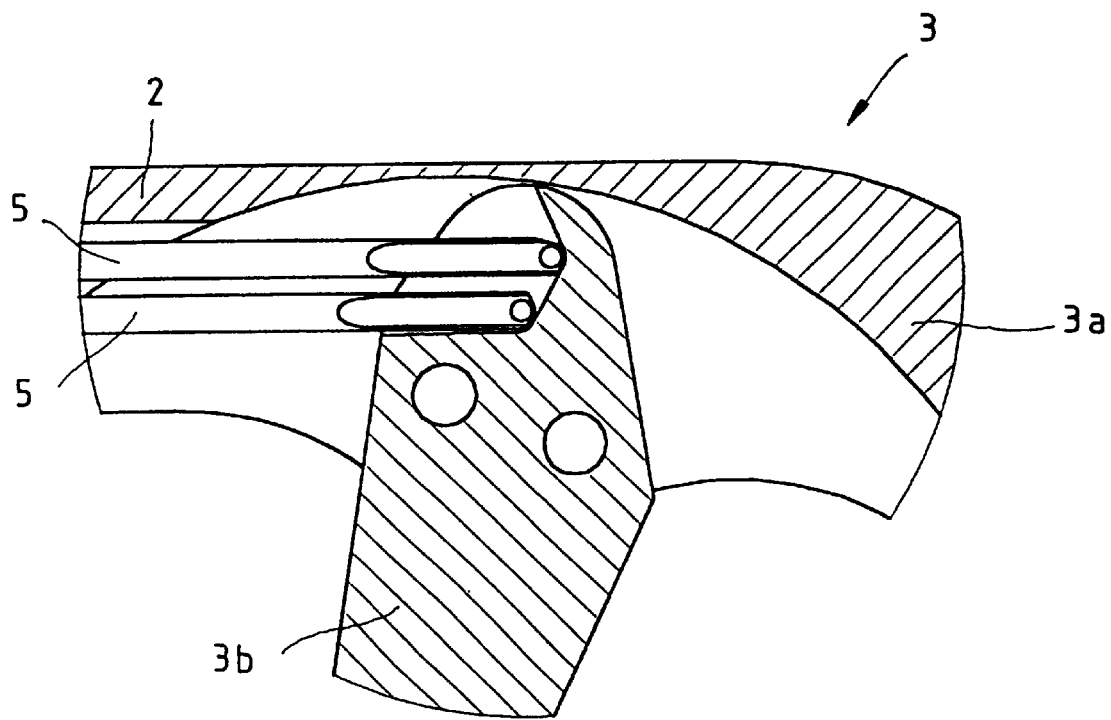
FIG. 2b is an enlarged and partially sectional view of detail IIb according to FIG. 1.
Figure 4A:
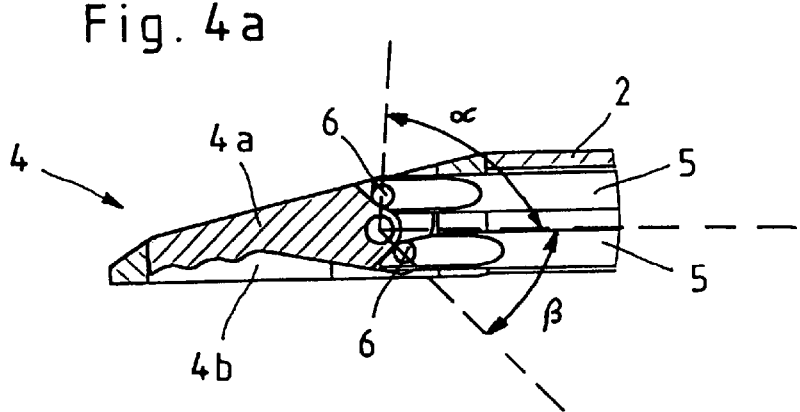
FIG. 4a is an enlarged and partially sectional view of detail IVa according to FIG. 3.
Figure 4B:
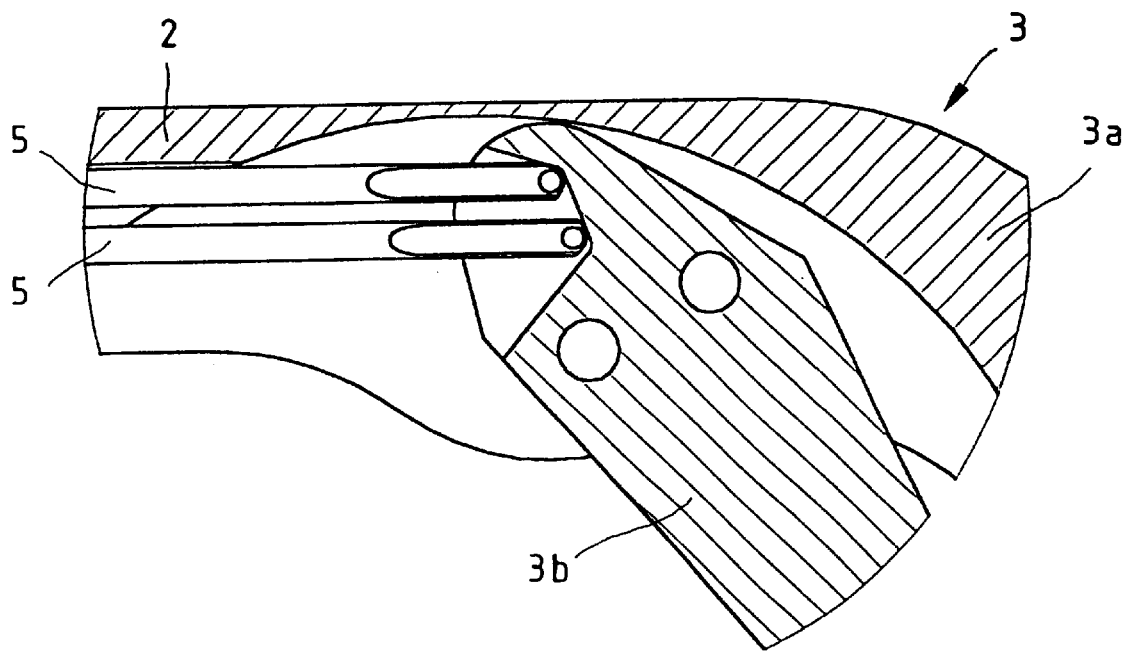
FIG. 4b is an enlarged and partially sectional view of detail IVb according to FIG. 3.

To achieve the best possible power transmission between the handle 3 and the adjustable jaw member 4a of the tool 4, the push/pull rods 5 are secured at a distance from one another, as can be seen from FIGS. 2a and 4a, at contact points 6 above and below the pivot point of the adjustable jaw member 4a on the adjustable jaw member 4a in such a way that a line drawn through contact points 6 and the pivot point forms an angle of about 110 to 160 degrees. Because of this arrangement of the push/pull rods 5, the upper push/pull rod 5 is activated to pull on opening the tool 4, while the lower push/pull rod is activated to push. In closing, the exact opposite is true; that is, now the upper push/pull rod 5 is activated to push and the lower part to pull. The transmission of power in the illustrated embodiment occurs essentially by means of the push/pull rod 5 activated to push in each case.

The lever ratios favorable to power transmission are also determined from the comparison of the angles formed between the longitudinal axis of the instrument 1 and a line through the contact points 6 of the push/pull rod 5 on the jaw member 4a and its pivot point. As can be seen from FIG. 2a, the angles in the open position are approximately alpha<beta [symbol: similar or equal to] 90 degrees In the closed position illustrated in FIG. 4a, the proportions are reversed, so that alpha [symbol: similar or equal to] 90 degrees>beta and thus independently of the extent of the opening for the at least one push/pull rod 5, in each case there is a nearly ideal lever ratio with an angle of about 90 degrees.

The medical instrument 1 is actuated as follows:

To ensure firm action of the gripping members 3a, 3b of the handle 3, these members have finger loops 3c on their free ends. In the illustrated embodiment, the gripping member 3b is rotatable in relation to the other, stationary gripping member 3a by means of a rotatable axis 7. The rotation path of the two gripping members 3a, 3b toward one another can be shortened by means of a transmission that is not shown in the illustration. It is also possible to configure both gripping members 3a, 3b of the handle 3 as rotatable gripping members.

The tool 4 can be opened and closed by means of the coupling of the rotatable gripping member 3b by the two push/pull rods 5 with the adjustable jaw member 4a. In addition to the illustrated embodiment with only one adjustable jaw member 4a, it is also possible of course to configure both jaw members 4a, 4b as adjustable. In this case a total of four push/pull rods 5 would be required, and both gripping members 3a, 3b of the handle 3 would have to be rotatable. The advantage of this non-illustrated embodiment is that the jaw members 4a, 4b can be closed at various angle settings to the shaft 2, so that the instrument 1 is more fully rotatable.

To facilitate cleaning and repair of the medical instrument 1, the push/pull rods 5 can be dissolubly connected with the jaw member 4a or with the gripping member 3b. Spring-activated groove connections and bayonet couplings are especially suited for this purpose.

A further possibility is to configure the turn joint 7 of the handle 3b in the form of spring-activated pressure buttons, which engage into corresponding hollows in the stationary gripping member 3a. After pressing these pressure buttons, the rotatable gripping member 3b can be removed from the stationary gripping member 3a and can be rotated outward together with the two push/pull rods 5 downward from the shaft 2 that is open at that point. This allows for a simple and thorough cleaning at low cost in order to dismantle the instrument 1.

The illustrated medical instrument 1 is distinguished in general in that it ensures a uniformly strong power transmission independently of the opening position of the jaw members, and it is possible to apply this power in controlled doses so that, after penetration of tough tissue, no uncontrolled breakthrough of the power-impacted jaw member ensues.

| Number Key | |
|---|---|
| 1 | medical instrument |
| 2 | shaft |
| 3 | handle |
| 3a | stationary gripping member |
| 3b | rotatable gripping member |
| 3c | finger loops |
| 4 | tool |
| 4a | adjustable jaw member |
| 4b | stationary jaw member |
| 5 | push/pull rod |
| 6 | contact point |
| 7 | rotation axis |
| alpha | angle |
| beta | angle |

What is claimed is:

1. Medical instrument with a hollow shaft having at its proximal end a handle consisting of at least two gripping members and at its distal end a tool consisting of at least two jaw members, where at least one of the jaw members of the tool is adjustable in relation to the at least one other jaw member of the tool for purposes of opening and closing by means of one rotatably shaped gripping member of the handle, and the at least one adjustable jaw member and the corresponding gripping member of the handle that serves to adjust the jaw member are connected to one another by means of two push-pull rods distinguished in that the two push/pull rods are secured on contact points at intervals from one another above and below the pivot point of the adjustable jaw member on this jaw member so that two straight lines each extending from the pivot point through one of the contact points form an angle (alpha+beta) of 110 to 160 degrees.

2. Medical instrument according to claim 1, distinguished in that the push/pull rods are removable from the shaft.

3. Medical instrument according to claim 2, distinguished in that the push/pull rods together with the respective gripping member of the handle are dissolubly connected with the stationary gripping member by means of a groove connection, in particular a spring-activated groove connection.

4. Medical instrument according to claim 1, distinguished in that the tool can be secured to the distal end of the shaft by means of a bayonet coupling and the push/pull pins can be separated from the gripping member.

5. Medical instrument according to claim 1, distinguished in that every push/pull rod is contained in a separate shaft.

6. Medical instrument according to claim 1, distinguished in that, between the gripping members of the handle that are rotatable toward one another, a transmission is installed in order to reduce the rotation path of the gripping members to one another.

7. Medical instrument according to claim 1, distinguished in that two jaw members of the tool are configured to be adjustable, so that every jaw member is respectively connected with one gripping member of the handle by means of two push/pull rods each, which rods are configured to be rotatable independently of one another.

* * * * *